United States Patent [19]

Vorbrueggen et al.

[11] 4,378,370
[45] Mar. 29, 1983

[54] CERTAIN 5-CYANO-16-FLUORO-PROSTACYCLINS AND THEIR USE AS PHARMACEUTICALS

[75] Inventors: Helmut Vorbrueggen; Bernd Raduechel; Werner Skuballa; Gerda Mannesmann; Jorge Casals-Stenzel; Ekkehard Schillinger, all of Berlin, Fed. Rep. of Germany

[73] Assignee: Schering Aktiengesellschaft, Berlin and Bergkamen, Fed. Rep. of Germany

[21] Appl. No.: 309,967

[22] PCT Filed: Feb. 5, 1981

[86] PCT No.: PCT/DE81/00031
§ 371 Date: Oct. 6, 1981
§ 102(e) Date: Oct. 6, 1981

[87] PCT Pub. No.: WO81/02296
PCT Pub. Date: Aug. 20, 1981

[30] Foreign Application Priority Data
Feb. 7, 1980 [DE] Fed. Rep. of Germany ....... 3004795

[51] Int. Cl.³ .................. A61K 31/34; C07D 307/935
[52] U.S. Cl. .................................. 424/285; 542/429; 549/465
[58] Field of Search .............. 260/346.22, 346.73; 542/429; 424/285

[56] References Cited
U.S. PATENT DOCUMENTS
4,219,479 8/1980 Vorbrueggen et al. ....... 260/346.22

Primary Examiner—John M. Ford
Assistant Examiner—Bernard Dentz
Attorney, Agent, or Firm—Millen & White

[57] ABSTRACT

Prostacyclin derivatives of the formula

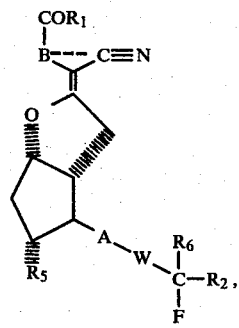

wherein
$R_1$ is $OR_3$ wherein $R_3$ is hydrogen or alkyl of 1–10 carbon atoms, or $R_1$ is $NHR_4$ wherein $R_4$ is alkanoyl or alkanesulfonyl,
B is alkylene of 1–5 carbon atoms,
A is —$CH_2$—$CH_2$—, cis—CH═CH—, or trans—CH═CH—,
W is hydroxymethylene or $$\begin{array}{c} CH_3 \\ | \\ -C- \\ | \\ OH \end{array}$$

wherein the OH-group is optionally substituted by alkanoyl of 1–4 carbon atoms and the free or substituted OH-group can be in the α- or β- position,
$R_2$ is alkyl of 1–6 carbon atoms optionally substituted by phenyl, or $R_2$ is phenyl,
$R_5$ is hydroxy optionally substituted by alkanoyl of 1–4 carbon atoms,
$R_6$ is hydrogen, fluorine, or alkyl of 1–4 carbon atoms or when $R_3$ is hydrogen, a salt thereof with a physiologically compatible base, have pharmacological activity e.g., blood pressure-lowering and bronchodilatory effects.

15 Claims, No Drawings

CERTAIN 5-CYANO-16-FLUORO-PROSTACYCLINS AND THEIR USE AS PHARMACEUTICALS

BACKGROUND OF THE INVENTION

The invention relates to novel prostacyclin derivatives, a process for the preparation thereof, as well as the utilization thereof as medicinal agents.

Prostacyclin ($PGI_2$), one of the primary factors in blood platelet aggregation, has a dilating effect on various blood vessels (Science 196, 1072) and thus can be considered a blood-pressure-lowering agent. However, $PGI_2$ does not have the stability required for a medicinal agent. Thus, the half-life value of $PGI_2$ at physiological pH values and at room temperature is only a few minutes. Prostacyclin is stabilized by the introduction of a nitrile group at the enol ether double bond, retaining the pharmacological spectrum of efficacy, and markedly prolonging the duration of activity (DOS No. 2,753,244). The additional introduction of fluorine in the 16-position effects a further increase in duration of effectiveness and selectivity.

SUMMARY OF THE INVENTION

The compounds of this invention have a blood-pressure-lowering effect and a bronchodilatory activity. Furthermore, these compounds are suitable for inhibition of thrombocyte aggregation and inhibition of gastric acid secretion.

The invention concerns prostane derivatives of general Formula I

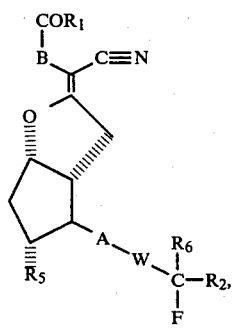

wherein
$R_1$ represents the residue $OR_3$ wherein $R_3$ can be hydrogen or alkyl of 1-10 carbon atoms, or $R_1$ is the residue $NHR_4$ wherein $R_4$ is an alkanoyl or alkanesulfonyl residue,
B is a straight-chain or branched-chain alkylene group of 1-5 carbon atoms,
A is a $-CH_2-CH_2-$, cis-$CH=CH-$, or trans-$CH=CH-$ group,
W is a hydroxymethylene group or a

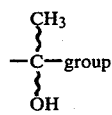

wherein the OH-group can be respectively substituted by alkanoyl of 1-4 carbon atoms and the free or substituted OH-group can be in the α- or β-position, $R_2$ is a saturated straight-chain or branched-chain alkyl group of 1-6 carbon atoms which can be substituted by phenyl, or a phenyl group,
$R_5$ is a hydroxy group which can be substituted by alkanoyl of 1-4 carbon atoms,
$R_6$ is hydrogen, fluorine, or alkyl of 1-4 carbon atoms and, if $R_3$ is hydrogen, the salts thereof with physiologically compatible bases.

DETAILED DISCUSSION

Suitable alkyl groups $R_3$ are straight-chain or branched-chain alkyl groups of 1-10 carbon atoms, e.g. methyl, ethyl, propyl, butyl, isobutyl, tert.-butyl, pentyl, neopentyl, heptyl, hexyl, decyl. Preferred alkyl groups $R_3$ are those of 1-4 carbon atoms, such as, for example, methyl, ethyl, propyl, isobutyl, butyl.

The alkanoyl residue $R_4$ can be constituted by physiologically acceptable acid residues derived from the following carboxylic acids: formic acid, acetic acid, propionic acid, butyric acid, isobutyric acid, valeric acid, isovaleric acid, caproic acid, enanthic acid, caprylic acid, pelargonic acid, capric acid, trimethylacetic acid, diethylacetic acid, tert.-butylacetic acid. The alkanesulfonyl residues $R_4$ are derived, for example, from methanesulfonic acid, ethanesulfonic acid, isopropanesulfonic acid, butanesulfonic acid.

Acetyl, propionyl, and butyryl can be named as alkanoyl residues in $R_5$ and W. Suitable as the alkyl group $R_2$ are straight-chain and branched-chain, saturated alkyl residues of 1-6 carbon atoms substitutable by phenyl, e.g. methyl, ethyl, propyl, butyl, isobutyl, tert.-butyl, phenyl, hexyl, and benzyl.

Suitable as the alkyl group $R_6$ are straight-chain and branched-chain, saturated alkyl residues of 1-4 carbon atoms. The following can be recited: methyl, ethyl, propyl, isopropyl, butyl, isobutyl, tert.-butyl.

The alkylene group B can be constituted by straight-chain, saturated alkylene residues of 1-5 carbon atoms, to wit, methylene, ethylene, trimethylene, tetramethylene, pentamethylene.

Inorganic and organic bases are suitable for the salt formation, as they are familiar to those skilled in the art for the formation of physiologically compatible salts. Examples are alkali hydroxides, such as sodium and potassium hydroxide, alkaline earth hydroxides, such as calcium hydroxide, ammonia, amines, such as ethanolamine, diethanolamine, triethanolamine, N-methylglucamine, morpholine, tris(hydroxymethyl)methylamine, etc.

The invention furthermore relates to a process for the preparation of the prostacyclin derivatives of general Formula I according to this invention, characterized by reacting in a manner known per se a compound of general Formula II

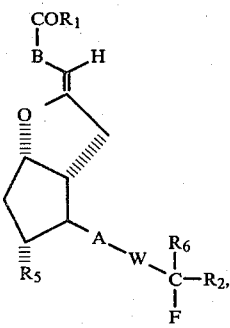

wherein R$_1$, R$_2$, R$_5$, R$_6$, A, B, and W have the meanings indicated above, optionally after blocking any free hydroxy groups present,
with a sulfonyl isocyanate of general Formula III $$R_7SO_2NCO \quad \quad III$$

wherein R$_7$ signifies a phenyl ring optionally substituted by alkyl of 1-4 carbon atoms, halogenated alkyl, or halogen,
and subsequently with a tertiary amine or tertiary amide.

If desired, it is possible in the thus-obtained products of the process to effect, in any desired sequence, liberation of blocked hydroxy groups and/or esterification, etherification, or oxidation of free hydroxy groups, and reaction of the thus-obtained carbonyl groups with methylmagnesium halides, saponification of an esterified carbonyl group, or esterification of a carbonyl group, reaction of a carboxyl group with compounds of general Formula IV $$O=C=N-R_4 \quad \quad IV$$

wherein R$_4$ has the above-indicated meanings, or conversion of a carboxyl group into a salt with a physiologically compatible base.

The reaction of the enol ethers II to the compounds of general Formula I is performed in succession in the same reaction vessel with sulfonyl isocyanates of Formula III and a tertiary amine in an inert solvent, preferably tetrahydrofuran, dioxane, diethyl ether, toluene, or tert.-amide, preferably without a solvent. The sulfonyl isocyanates of general Formula III can be benzenesulfonyl isocyanate, p-toluenesulfonyl isocyanate, as well as the halosulfonyl isocyanates with the halogens fluorine, chlorine, and bromine. Chlorosulfonyl isocyanate is especially preferred for the reaction with compounds of Formula II.

The reaction with sulfonyl isocyanates of Formula III takes place at temperatures of between 30° and −100° C., preferably between −70° and 0° C. The reaction with a tertiary amine or tertiary amide is conducted at temperatures of between −100° and 30° C., preferably between −70° and +30° C. Examples for tertiary amines are: triethylamine, trimethylamine, diethylisopropylamine, dimethylisopropylamine, DBN, DBU, etc.

Dimethylformamide is the preferred tertiary amide.

The saponification of the prostacyclin esters is conducted according to methods known to those skilled in the art, e.g. with basic catalysts.

The ester group —OR$_3$ for R$_1$ wherein R$_3$ is an alkyl group of 1-10 carbon atoms is introduced according to methods known to persons skilled in the art. The carboxy compounds are reacted, for example, with diazohydrocarbons in a manner known per se. The esterification with diazohydrocarbons is accomplished, for example, by mixing a solution of the diazohydrocarbon in an inert solvent, preferably in diethyl ether, with the carboxy compound in the same or another inert solvent, e.g. methylene chloride. After the reaction is finished in 1-30 minutes, the solvent is removed and the ester purified as usual. Diazoalkanes are either known or can be produced according to the conventional methods [Org. Reactions 8: 389-394 (1954)].

The prostacyclin derivatives of general Formula I with R$_1$ meaning a hydroxy group can be converted into salts with suitable amounts of the corresponding inorganic bases under neutralization. For example, the solid inorganic salt is obtained when dissolving the corresponding acids in water containing the stoichiometric quantity of the base, after removal of the water by evaporation or after the addition of a water-miscible solvent, for example alcohol or acetone.

To produce an amine salt, which is done in the usual way, the acid is dissolved, for example, in an inert solvent, e.g. ethanol, acetone, diethyl ether, or benzene, and at least the stoichiometric amount of the amine is added to this solution. During this tep, the salt is ordinarily obtained in the solid form or is isolated in the usual way after evaporation of the solvent.

The acyl blocking group is introduced by reacting a compound of general Formula I in a manner known per se with a carboxylic acid derivative, e.g. an acid chloride, an acid anhydride, and others.

The liberation of a functionally modified OH-group in the compounds of general Formula I takes place according to conventional methods.

The acyl groups are saponified, for example, with alkali or alkaline earth carbonates or hydroxides in an alcohol or in the aqueous solution of an alcohol. Suitable alcohols are aliphatic alcohols, e.g. methanol, ethanol, butanol, etc., preferably methanol. Alkali carbonates and hydroxides can be potassium and sodium salts, but preferably the potassium salts. Suitable as alkaline earth carbonates and hydroxides are, for example, calcium carbonate, calcium hydroxide, and barium carbonate. The reaction takes place at −10° to 70° C., preferably at 25° C.

The reaction of the compound of general Formula I with R$_3$ meaning a hydrogen atom with an isocyanate of general Formula IV takes place optionally with the addition of a tertiary amine, e.g. triethylamine or pyridine. The reaction can be performed without a solvent or in an inert solvent, preferably acetonitrile, tetrahydrofuran, acetone, dimethylacetamide, methylene chloride, diethyl ether, benzene, toluene, dimethyl sulfoxide, at temperatures above or below room temperature, for example between −80° to 100° C., preferably at 0° to 30° C.

If the starting compound contains OH-groups in the prostane residue, these OH-groups are likewise reacted. If final products are lastly desired which contain free hydroxy groups in the prostane residue, it is advantageous to utilize starting compounds wherein these groups are intermediarily blocked by preferably readily cleavable ether or acyl residues.

The oxidation of the 15-OH-group with manganese dioxide has been described in "Reagents for Organic Synthesis", Fieser and Fieser 1:637, J. Wiley N.Y. 1967.

The subsequent Grignard reaction with methylmagnesium halides is accomplished according to methods known to those skilled in the art.

The compounds of general Formula II serving as the starting material can be produced, for example, by reacting, in a manner known per se, a conventional prostaglandin F derivative of the general Formula V

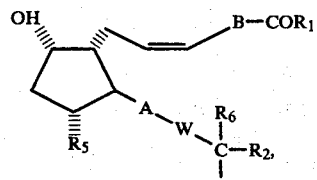

with iodine in the presence of an alkali hydrogen carbonate or alkali carbonate to obtain the compounds of general Formula VI

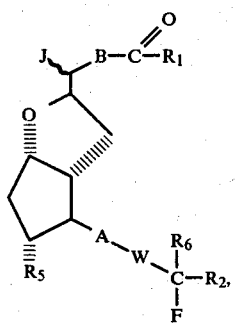

wherein, in V and VI, $R_1$, $R_2$, $R_5$, $R_6$, A, B, and W have the same meanings as indicated above.

If desired, free hydroxy groups can subsequently be blocked by esterification or introduction of the silyl group. Depending on the desired significance of A or $R_1$ in the final products of general Formula I, double bonds in VI can optionally be hydrogenated or, if desired, a carboxy group can be esterified or a carboxy group can be reacted with compounds of general Formula IV.

The splitting off of the silyl ether blocking groups takes place, for example, with tetrabutylammonium fluoride. Examples for suitable solvents are tetrahydrofuran, diethyl ether, dioxane, methylene chloride, etc. The splitting off step is preferably performed at temperatures of between 0° and 80° C.

The reaction of the compounds of general Formula VI to the compounds of general Formula II can be accomplished, for example, with 1,5-diazabicyclo[4.3.0]nonene-5 (DBN) or 1,5-diazabicyclo[5.4.0]undecene-5 (DBU) in an inert solvent, such as benzene, toluene, tetrahydrofuran, etc., or with sodium methylate in methanol. The splitting off of hydrogen halide is effected at temperatures of between 0° and 120° C., preferably at 20°-60° C.

The novel prostacyclin derivatives of general Formula I are valuable pharmaceuticals, since they are distinguished, with a similar spectrum of effectiveness, over corresponding prostaglandins by higher specificity and, above all, a substantially longer-lasting efficacy. As compared with PGE, PGA, and PGI, the novel prostaglandins excel by higher stability. The good tissue specificity of the novel prostaglandins is demonstrated in a study on smooth-muscle organs, such as, for example, on the guinea pig ileum or the guinea pig uterus, where a substantially lesser stimulation can be observed than in the administration of natural prostaglandins.

The novel prostaglandin analogs possess the pharmacological characteristics typical for prostaglandins, such as, for example, lowering of the blood pressure, inhibition of thrombocyte aggregation, inhibition of gastric acid secretion, bronchodilatory properties, and others. The claimed compounds are administered for the above-mentioned effects in dosage ranges from 5 to 5000 μg/kg/day.

The novel prostacyclin derivatives of general Formula I possess an increased stability as compared with $PGI_2$. With a comparable ulcer inhibition in indomethacin-induced ulceration, the novel compounds exert a lesser influence on blood pressure and thrombocyte aggregation than $PGI_2$.

Upon intravenous injection given to nonanesthetized, hypertonic rats in doses from 10 to 150 μg/kg body weight, the compounds of this invention show a stronger blood-pressure-lowering effect than $PGE_2$ and $PGA_2$, without triggering, in these dosages, diarrhea, as would $PGE_2$, or causing cardiac arrhythmias, as would $PGA_2$.

Upon intravenous injection given to narcotized rabbits, the compounds of this invention show, as compared with $PGE_2$ and $PGA_2$, a stronger and substantially more prolonged lowering of the blood pressure, without effect on other smooth-muscle organs or organ functions.

Aerosol preparations are provided for asthma therapy.

Sterile, injectable aqueous or oily solutions are utilized for parenteral administration.

Tablets, dragees, or capsules are suitable, for example, for oral administration.

The invention accordingly also concerns medicinal agents on the basis of the compounds of general Formula I and customary excipients and vehicles.

The active agents of this invention are to serve, in conjunction with the auxiliary agents known and usual in galenic pharmacy, for example for the preparation of blood-pressure-lowering agents and asthma medicines.

EXAMPLE 1

5-Cyano-16-fluoroprostacyclin Methyl Ester 11,15-Diacetate

Under argon, 262 mg of chlorosulfonyl isocyanate, dissolved in 5 ml of ether, is added dropwise at −70° C. to a solution of 773 mg of 16-fluoroprostacyclin methyl ester 11,15-diacetate in 5 ml of ether. After 15 minutes, the mixture is combined with 6 ml of dimethylformamide and stirred for 2 hours at 20° C. The mixture is then diluted with 100 ml of ice-cold 5% sodium bicarbonate solution and extracted three times with respectively 100 ml of ether. The organic phase is shaken with 30 ml of brine, dried over magnesium sulfate, and evaporated under vacuum. For purification, the mixture is chromatographed on a silica gel column, eluting with hexane-ether mixtures. Yield: 430 mg of the title compound as an oil.

IR: 2955, 2858, 2200, 1730, 1650, 1280, 970 cm$^{-1}$.

The starting material for the title compound is prepared as follows:

1(a) 5,6-Dihydro-16-fluoro-5-iodoprostacyclin Methyl Ester

A mixture of 2 g of 16-fluoroprostaglandin $F_{2\alpha}$ methyl ester (prepared according to DOS 2,320,368), 5.3 g of sodium bicarbonate, 50 ml of ether, and 90 ml of water is combined at 0° C. within 3 hours under agitation with 65 ml of a 2.5% ethereal iodine solution. The mixture is stirred for 22 hours at 0° C., diluted with 250 ml of ether, shaken with sodium thiosulfate solution and brine, dried over magnesium sulfate, and evaporated under vacuum, thus obtaining 2.5 g of the title compound as an oil.

IR: 3600, 3420 (broad), 2955, 1730, 972 cm$^{-1}$.

1(b) 5,6-Dihydro-16-fluoro-5-iodoprostacyclin Methyl Ester 11,15-Diacetate 2.5 g of the compound prepared according to Example 1(a) is dissolved in 10 ml of pyridine and 5 ml of acetic anhydride, allowed to stand for 18 hours at 20° C., evaporated under vacuum, combined with 5 ml of toluene, again evaporated, and 3.1 g of the title compound is thus obtained as an oil.

IR: 2955, 1735, 1260, 974 cm$^{-1}$.

1(c) 16-Fluoroprostacyclin Methyl Ester 11,15-Diacetate 1.20 g of the compound prepared according to Example 1(b) is dissolved in 12 ml of benzene, combined with 6 ml of 1,5-diazabicyclo[4.3.0]non-5-ene and heated under argon for 24 hours to 50° C. The mixture is cooled, diluted with 400 ml of ether, shaken three times with respectively 15 ml of ice water, dried over sodium sulfate, and evaporated at 25° C. under vacuum. The thin-layer chromatogram on silica gel plates (eluent: ether) shows a main spot ($R_f$ value 0.62) and a minor more polar impurity ($R_f$ value 0.45). Yield: 1.02 g. The preparation is used without further purification.

EXAMPLE 2

5-Cyano-16-fluoroprostacyclin Methyl Ester 400 mg of 5-cyano-16-fluoroprostacyclin methyl ester 11,15-diacetate (prepared according to Example 1), 240 mg of potassium carbonate, and 15 ml of methanol are stirred for 3 hours at 25° C. under argon. The mixture is then diluted with 200 ml of ether, washed three times with respectively 20 ml of water, dried over sodium sulfate, and evaporated under vacuum, thus obtaining 290 mg of the title compound as an oil.

IR: 3600, 3420, 2950, 2862, 2205, 1735, 1650, 974 cm$^{-1}$.

EXAMPLE 3

5-Cyano-16-fluoroprostacyclin

A solution of 120 mg of 5-cyano-16-fluoroprostacyclin methyl ester (see Example 2) in 10 ml of methanol is combined with 1 ml of 1 N sodium hydroxide solution, agitated for 2 hours at 25° C., evaporated under vacuum, mixed with 20 ml of brine and 10 ml of citrate buffer (pH 6.5), and extracted four times with respectively 25 ml of methylene chloride. The organic phase is shaken with 10 ml of brine, dried over magnesium sulfate, and evaporated under vacuum at 25° C., thus obtaining 100 mg of the title compound as an oil. The thin-layer chromatogram on silica gel plates using as eluent methylene chloride/methanol (8+2) shows only one spot with the $R_f$ value of 0.42.

IR: 3602, 3420, 2948, 2858, 2205, 1710, 1650, 976 cm$^{-1}$.

EXAMPLE 4

5-Cyano-16-fluoro-20-methylprostacyclin Methyl Ester 11,15-Diacetate 485 mg of 16-fluoro-20-methylprostacyclin methyl ester 11,15-diacetate is dissolved in 4 ml of ether; under argon at −70° C., a solution of 169 mg of chlorosulfonyl isocyanate in 3 ml of ether is added dropwise thereto, the mixture is stirred for 10 minutes, combined with 3 ml of dimethylformamide, and agitated for 2 hours at 20° C. The mixture is then diluted with 60 ml of ice-cold sodium bicarbonate solution (5% strength), extracted three times with respectively 75 ml of ether, the organic phase washed with 20 ml of brine, dried over magnesium sulfate, and evaporated under vacuum. The product is purified by chromatography on silica gel; with hexane/ether (2:1), 300 mg of the oily title compound is eluted.

IR: 2950, 2860, 2205, 1730, 1650, 1265, 972 cm$^{-1}$.

The starting material for the title compound is produced as follows:

4(a) 5,6-Dihydro-16-fluoro-5-iodo-20-methylprostacyclin Methyl Ester 1.5 g of 16-fluoro-20-methylprostaglandin methyl ester (prepared according to DOS 2,320,368) is dissolved in 35 ml of ether, combined with 70 ml of water and 4 g of sodium bicarbonate, and 48 ml of a 2.5% ethereal iodine solution is added dropwise under agitation at 0° C. within 2 hours. The mixture is stirred for another 20 hours at 0° C., diluted with 200 ml of ether, shaken in succession with sodium thiosulfate solution and brine, dried over magnesium sulfate, and evaporated under vacuum, thus obtaining 1.95 g of the title compound as an oil.

IR: 3605, 3400 (broad), 2956, 1735, 974 cm$^{-1}$.

4(b) 5,6-Dihydro-16-fluoro-5-iodo-20-methylprostacyclin Methyl Ester 11,15-Diacetate The procedure of Example 1(b) is employed, thus producing from 1.90 g of the diol prepared according to Example 4(a) 2.35 of crude diacetate which is purified by chromatography on silica gel. By elution with hexane/ethyl acetate (1:1), 2.05 g of the pure title compound is produced as an oil.

IR: 2952, 1735, 1275, 978 cm$^{-1}$.

4(c) 16-Fluoro-20-methylprostacyclin Methyl Ester 11,15-Diacetate

A solution of 1.5 g of the diacetate prepared according to Example 4(b) in 15 ml of benzene and 8 ml of 1,5-diazabicyclo[4.3.0]non-5-ene is heated for 18 hours to 55° C. under argon. The mixture is then cooled to 0° C., diluted with 500 ml of ether, shaken several times with a small amount of ice water, dried over sodium sulfate, and evaporated under vacuum at 25° C. Yield: 1.2 g of the title compound as an oil, which is utilized without further purification for introduction of the nitrile group.

EXAMPLE 5

5-Cyano-16-fluoro-20-methylprostacyclin Methyl Ester 200 mg of 5-cyano-16-fluoro-20-methylprostacyclin methyl ester 11,15-diacetate, dissolved in 8 ml of methanol, is stirred with 220 mg of potassium carbonate for 3 hours at 20°–25° C. Thereafter, the mixture is diluted with 150 ml of ether, shaken three times with respectively 15 ml of water, dried over sodium sulfate, and evaporated under vacuum, thus obtaining 140 mg of the title compound as an oil.

IR: 3600, 3410, 2962, 2860, 2205, 1735, 1652, 976 cm$^{-1}$.

EXAMPLE 6

5-Cyano-16-fluoro-20-methylprostacyclin 100 mg of 5-cyano-16-fluoro-20-methylprostacyclin methyl ester (prepared according to Example 5) is dissolved in 5 ml of methanol, combined with 1 ml of 1 N sodium hydroxide solution and stirred for 2 hours at 25° C. under argon. The mixture is then evaporated under vacuum, the residue dissolved in 20 ml of brine, combined with 10 ml of citrate buffer (pH 6.5), extracted several times with methylene chloride, the organic phase washed once with a small amount of brine, dried over magnesium sulfate, and evaporated under vacuum. Yield: 85 mg of the title compound as an oil.

IR: 3600, 3420, 2954, 2860, 2202, 1708, 1650, 978 cm$^{-1}$.

The thin-layer chromatogram of the compound on silica gel plates with methylene chloride-methanol (8+2) as the eluent shows only one spot, R$_f$ value: 0.47.

EXAMPLE 7

5-Cyano-16-fluoro-15-methylprostacyclin

A solution of 200 mg of 5-cyano-15-dehydro-16-fluoroprostacyclin methyl ester in a mixture of 5 ml of ether and 5 ml of tetrahydrofuran is combined at −100° C. under argon with 1.5 ml of a 1-molar ethereal methylmagnesium bromide solution within 20 minutes. After another 20 minutes at −70° C., ice pieces are added, the mixture is heated to 0° C., combined with citrate buffer (pH 6), and repeatedly extracted with methylene chloride. The combined extracts are washed with a small amount of brine and evaporated under vacuum. The residue is dissolved in 5 ml of methanol, combined with 1 ml of 1 N sodium hydroxide solution, agitated for two hours at 20° C., and evaporated under vacuum. Thereafter the mixture is diluted with citrate buffer (pH 6), extracted with methylene chloride, the extract washed with brine, dried over magnesium sulfate, and evaporated under vacuum. The residue is purified by chromatography on silica gel. With methylene chloride/5% isopropanol, 80 mg of the title compound is eluted as an oil IR: 3600, 3420, 2952, 2860, 2202, 1708, 1650, 978 cm$^{-1}$.

The starting material for the title compound is prepared as follows:

7(a) 5-Cyano-15-dehydro-16-fluoroprostacyclin Methyl Ester

A solution of 500 mg of 5-cyano-16-fluoroprostacyclin methyl ester in 20 ml of ether is combined with 5 g of manganese dioxide and stirred for four hours at 20° C. This slurry is introduced into a silica gel column (1.5×20 cm) and washed with 200 ml of ether. After evaporation of the eluate, 220 mg of the title compound is obtained as an oil.

IR: 3600, 2950, 2862, 2205, 1732, 1695, 1628, 978 cm$^{-1}$.

EXAMPLE 8

5-Cyano-16-fluoro-16-methylprostacyclin

A solution of 255 mg of 3-fluoro-3-methyl-2-oxoheptanephosphonic acid dimethyl ester in 10 ml of dimethoxyethane is added dropwise to a suspension of 48 mg of 50% sodium hydride in 5 ml of dimethoxyethane under argon, stirred for one hour at 20° C., then cooled to 0° C., and a solution of 320 mg of the methyl ester of 5-{(E)-(1S,5R,6R,7R)-7-acetoxy-6-formyl-2-oxabicyclo[3.3.0]octan-3-ylidene}-5-cyanopentanoic acid in 5 ml of dimethoxyethane is added dropwise within 5 minutes; the reaction mixture is agitated for another hour at 10° C., diluted with 150 ml of citrate buffer (pH 6), extracted three times with respectively 40 ml of ether, the organic phase washed with 10 ml of brine, dried over magnesium sulfate, and evaporated under vacuum. The residue is dissolved in 20 ml of an ethanol-tetrahydrofuran mixture (1:1), cooled to −40° C., and combined with 1 g of sodium borohydride. Under agitation, the temperature is maintained at −40° C. and the progress of the reaction is observed by thin-layer chromatography on silica gel plates (eluent: toluene-ethyl acetate 7+3). After two hours, the mixture is diluted with 100 ml of citrate buffer (pH 6), extracted three times with respectively 40 ml of methylene chloride, the combined extracts are shaken with 10 ml of brine, dried over magnesium sulfate, and evaporated under vacuum. The thin-layer chromatogram (toluene-ethyl acetate 8+2, eluted twice) shows two spots of the C-15 epimeric alcohols with the R$_f$ values of 0.39 and 0.45. For separation purposes, the mixture is chromatographed on a silica gel column (1.5×50 cm) and eluted with hexane and rising ethyl acetate gradients, thus obtaining 140 mg of 5-cyano-16-fluoro-16-methylprostacyclin methyl ester as an oil. For saponifying, the product is dissolved in 4 ml of methanol and 1 ml of 1 N sodium hydroxide solution, agitated for two hours at 25° C., evaporated at 25° C. under vacuum so that the largest portion of the solvent is removed, diluted with 50 ml of citrate buffer (pH 6), extracted three times with respectively 30 ml of methylene chloride, the combined organic phase is washed with 10 ml of brine, dired over magnesium sulfate, and evaporated under vacuum, thus obtaining 115 mg of the title compound in the form of an oil.

IR: 3600, 3420, 2952, 2860, 2204, 1708, 1650, 978 cm$^{-1}$.

The starting material for the title compound is prepared as follows:

8(a)

(1S,5R,6S,7R)-7-Benzoyloxy-6-(tert.-butyldimethylsilyloxy)methyl-2-oxabicyclo[3.3.0]octan-3-one A solution of 16.58 g of (1S,5R,6S,7R)-7-benzoyloxy-6-hydroxymethyl-2-oxabicyclo[3.3.0]octan-3-one in 18 ml of dimethylformamide is combined at 0° C. with 10.21 g of imidazole and 10.85 g of tert.-butyldimethylsilyl chloride. The mixture is stirred for 24 hours at 20° C., diluted with 1.5 l of ether, shaken in succession with 5% sulfuric acid and brine, dried over magnesium sulfate, and evaporated under vacuum. The residue is recrystallized from hexane.

Yield: 20 g of colorless crystals, mp 75° C.

IR: 2955, 2930, 2858, 1770, 1712, 1272, 1108, 834 cm$^{-1}$.

8(b)
(1S,3RS,5R,6S,7R)-6-(tert.-Butyldimethylsilyloxy)-methyl-2-oxabicyclo[3.3.0]octane-3,7-diol Under agitation at −70° C., 75 ml of a 20% solution of diisobutylaluminum hydride in toluene is added dropwise within 20 minutes to a solution of 10 g of the compound prepared according to Example 8(a) in 400 ml of toluene; after another 15 minutes, the mixture is combined with 5 ml of isopropanol, then with 40 ml of water, and stirred for one hour at room temperature. Subsequently, the mixture is filtered, the precipitate is washed with methylene chloride, and the solution is evaporated under vacuum. To remove benzaldehyde and benzyl alcohol, the mixture is chromatographed with hexane-ethyl acetate mixtures over silica gel, thus obtaining 7.1 g of the title compound as an oil.

IR: 3600, 3410, 2950, 2860, 1110, 835 cm$^{-1}$.

8(c)
(5Z)-7-[(1R,2S,3R,5S)-2-(tert.-Butyldimethylsilyloxy)-methyl-3,5-dihydroxycyclopentyl]-5-heptenoic Acid Methyl Ester 11.52 g of 50% sodium hydride is freed of mineral oil by treatment with pentane and stirred with 100 ml of dimethyl sulfoxide at 70° C. for 1.5 hours. The resultant solution of dimesyl sodium is added dropwise to 53.4 g of 4-carboxybutyltriphenylphosphonium bromide, dissolved in 400 ml of dimethyl sulfoxide, and then stirred for 30 minutes at 20° C. To the thus-obtained orange-red ylene solution, a solution is dropped of 7 g of the compound obtained according to Example 8(b) in 100 ml of dimethyl sulfoxide and agitated for three hours at 50° C. To work up the reaction mixture, the latter is diluted with 3 l of brine and extracted with 500 ml of ether. This extract contains primarily triphenylphosphine oxide. The aqueous phase is adjusted to pH 5 with citric acid and extracted three times with ether; the extract is shaken with brine and dried over magnesium sulfate, evaporated under vacuum. The residue is dissolved for esterifying in methylene chloride and treated at 0° C. with ethereal diazomethane solution, then evaporated under vacuum. For purification purposes, the product is chromatographed on silica gel with methylene chloride and the result is 7.9 g of the title compound as an oil.

IR: 3600, 1735, 1110, 835 cm$^{-1}$.

8(d)
(1S,3RS,5R,6S,7R)-3-[(1RS)-1-Iodo-4-methoxycarbonyl-1-butyl]-6-(tert.-butyldimethylsilyloxy)methyl-2-oxabicyclo[3.3.0]octan-7-ol Under agitation at 0° C., a solution of 6.1 g of iodine in 300 ml of ether is added dropwise within 4 hours to a mixture of 7 g of the compound obtained according to Example 8(c), 25 g of sodium bicarbonate, 200 ml of ether, and 200 ml of water; the mixture is then stirred for another 20 hours at 0° C., shaken in succession with sodium thiosulfate solution and brine, dried over magnesium sulfate, and evaporated under vacuum, thus obtaining 9 g of the oily title compound.

IR: 3600, 2955, 2860, 1732, 1105, 834 cm$^{-1}$.

8(e)
(1S,3RS,5R,6S,7R)-3-[(1SR)-1-Iodo-4-methoxycarbonyl-1-butyl]-6-(tert.-butyldimethylsilyloxy)methyl-7-acetoxy-2-oxabicyclo[3.3.0]octane 8 g of the compound obtained according to Example 8(d) is dissolved in 20 ml of pyridine, combined with 8 ml of acetic anhydride and allowed to stand for 20 hours at 20° C. The mixture is then evaporated under vacuum and the residue purified by chromatography on silica gel with hexane-ethyl acetate (3:1), thus obtaining 7.5 g of the title compound as an oil.

IR: 2960, 2858, 1735, 1105, 834 cm$^{-1}$.

8(f)
5-{(Z)-(1S,5R,6S,7R)-7-Acetoxy-6-(tert.-butyldimethylsilyloxy)methyl-2-oxabicyclo[3.3.0]octan-3-ylidene}pentanoic Acid Methyl Ester 7.5 g of the compound produced according to Example 8(e) is dissolved in 100 ml of toluene and 50 ml of 1,5-diazabicyclo[4.3.0]non-5-ene and heated under argon to 50° C. for 20 hours. The mixture is cooled, diluted with 1 liter of ether, and shaken three times with respectively 75 ml of ice water for extracting purposes. The product is dried over magnesium sulfate and evaporated under vacuum at 25° C.

8(g)
5-{(E)-(1S,5R,6S,7R)-7-Acetoxy-6-(tert.butyldimethylsilyloxy)methyl-2-oxabicyclo[3.3.0]octan-3-ylidene}-5-cyanopentanoic Acid Methyl Ester At −70° C. under argon, 2.75 g of chlorosulfonyl isocyanate, dissolved in 50 ml of ether, is added dropwise within 45 minutes to a solution of the compound obtained according to Example 8(f) in 75 ml of ether; the mixture is then combined with 50 ml of dimethylformamide and, after 10 minutes, with 10 ml of triethylamine, and thereafter stirred for 1 hour at −10° C., then diluted with 500 ml of 5% sodium bicarbonate solution, and extracted three times with respectively 200 ml of ether. The organic phase is shaken with 50 ml of brine, dried over magnesium sulfate, and evaporated under vacuum at 25° C. The product is purified by chromatography on silica gel, thus eluting with hexane-ether mixtures 1.95 g of the title compound as an oil.

IR: 2955, 2862, 2210, 1735, 1648, 1265, 1110, 834 cm$^{-1}$.

8(h)
5-{(E)-(1S,5R,6S,7R)-7-Acetoxy-6-hydroxymethyl-2-oxabicyclo[3.3.0]octan-3-ylidene}-5-cyanopentanoic Acid Methyl Ester 800 mg of tetrabutylammonium fluoride is added to a solution of 1.50 g of the compound prepared according to Example 8(g) in 50 ml of tetrahydrofuran, and the mixture is stirred for 4 hours at 20° C. Then the mixture is diluted with 100 ml of ether, shaken three times with respectively 10 ml of brine, dried over magnesium sulfate, and evaporated under vacuum. The residue is purified by chromatography on silica gel. With hexane-ethyl acetate (1:2), 800 mg of the title compound is eluted as an oil.

IR: 3580, 2950, 2862, 2208, 1735, 1648, 1262 cm$^{-1}$.

8(i)
5-{(E)-(1S,5R,6R,7R)-7-Acetoxy-6-formyl-2-oxabicyclo[3.3.0]octan-3-ylidene}-5-cyanopentanoic Acid Methyl Ester 3.5 g of Collins reagent (Organic Synthesis 52:5) is dissolved in 50 ml of methylene chloride. Under agitation, the mixture is combined with a solution of 800 mg of the compound produced according to Example 8(h) in 10 ml of methylene chloride, at 10° C. The mixture is stirred for another 15 minutes, diluted with 200 ml of ether, decanted, and the organic phase is shaken in succession twice with respectively 20 ml of 10% sulfuric acid, twice with respectively 20 ml of 5% sodium bicarbonate solution, and twice with 20 ml of brine, dried over magnesium sulfate, and evaporated under vacuum at 25° C.

Yield: 620 mg of the title compound as an oil.

IR: 2952, 2860, 2740, 2205, 1730, 1720 (shoulder), 1648, 1260 cm$^{-1}$.

EXAMPLE 9
5-Cyano-16-fluoro-N-methanesulfonylprostacyclin Carboxamide 400 mg of 5-cyano-16-fluoroprostacyclin (see Example 3) is dissolved in 2 ml of pyridine and 1 ml of acetic anhydride and allowed to stand for 12 hours at 25° C., whereafter the mixture is evaporated under vacuum. The residue is dissolved in 10 ml of acetonitrile, combined with 130 mg of triethylamine and then with a solution of 160 mg of methylsulfonyl isocyanate in 10 ml of acetonitrile. After 4 hours, the mixture is concentrated under vacuum, combined with citrate buffer (pH 6), and extracted with ether. The organic phase is shaken with brine, dried over magnesium sulfate, and evaporated under vacuum. The residue is dissolved in 10 ml of methanol and stirred for 2 hours with 250 mg of potassium carbonate. The mixture is then diluted with brine, adjusted to pH 6 with citric acid, and extracted repeatedly with methylene chloride, dried over magnesium sulfate, and evaporated under vacuum. The residue is purified by chromatography on silica gel. Elution with methylene chloride/5% isopropanol yields 150 mg of the title compound as an oil.

IR: 3410, 2950, 2862, 2205, 1718, 1650, 978 cm$^{-1}$.

EXAMPLE 10
5-Cyano-16-fluoro-20-methyl-N-acetylprostacyclin Carboxamide 205 mg of 5-cyano-16-fluoro-20-methylprostacyclin (preparation, see Example 6), 1.5 ml of pyridine, and 0.5 ml of acetic anhydride are stirred for 16 hours at 20° C., and then evaporated under vacuum. The residue is dissolved in 6 ml of acetonitrile, combined with 80 mg of triethylamine, and at 0° C. a solution of 58 mg of acetylisocyanate in 10 ml of acetonitrile is added dropwise thereto. The mixture is then stirred for 2 hours at 20° C., concentrated under vacuum, diluted with 50 ml of citrate buffer (pH 6.5), and extracted three times with respectively 40 ml of ether. The combined extracts are shaken with 10 ml of brine, dried over magnesium sulfate, and evaporated under vacuum. To split off the acetate groups, the mixture is dissolved in 5 ml of methanol and agitated for 2 hours at 20° C. with 110 mg of potassium carbonate, then diluted with 75 ml of brine, adjusted to pH 6.5 by adding citric acid, and repeatedly extracted with respectively 30 ml of methylene chloride; the extract is washed with 10 ml of brine and dried over magnesium sulfate. The residue from the evaporation is chromatographed on silica gel, eluting with methylene chloride/1% isopropyl alcohol. Yield: 85 mg of the title compound as an oil.

IR: 3600, 3410, 2960, 2858, 2204, 1735, 1705, 1648, 976 cm$^{-1}$.

EXAMPLE 11
5-Cyano-16,16-difluoroprostacyclin

A solution of 260 mg of 3,3-difluoro-2-oxoheptanephospnonic acid dimethyl ester [Prostaglandins 9:527 (1975)] in 10 ml of dimethoxyethane is added dropwise to a suspension of 48 mg of sodium hydride (50% mixture in mineral oil) in 5 ml of dimethoxyethane under argon. The mixture is stirred for one hour at 0° C., then at 0° C. a solution of 320 mg of 5-{(E)-(1S,5R,6R,7R)-7-acetoxy-6-formyl-2-oxabicyclo[3.3.0]octan-3-ylidene}-5-cyanopentanoic acid methyl ester [see Example 8(i)] in 5 ml of dimethoxyethane is added dropwise within 5 minutes, the mixture is stirred for another hour at 20° C., diluted with citrate buffer (pH 6), extracted with ether, the organic phase washed with brine, dried over magnesium sulfate, and evaporated under vacuum, yielding 15-dehydro-16,16-difluoro-5-cyanoprostacyclin methyl ester 11-acetate. To reduce the 15-keto group, the residue is dissolved in 10 ml of methanol and combined at −40° C. with 0.8 g of sodium borohydride. The mixture is stirred for two hours at −40° C., diluted with citrate buffer (pH 5), and extracted with methylene chloride, the organic phase washed with brine, dried over magnesium sulfate, and evaporated under vacuum. The residue is treated with 1 N sodium hydroxide solution in methanol (see Example 3), and the resultant product is purified by preparative thin-layer chromatography on silica gel plates (2.5 mm) developed with chloroform/isopropanol (7+3). The more polar zone is scraped off the plate and eluted with chloroform/isopropanol (9+1), thus obtaining 90 mg of the title compound as an oil.

IR: 3600, 3410, 2955, 2862, 2210, 1710, 1652, 972 cm$^{-1}$.

We claim:

1. A prostacyclin derivative of the formula

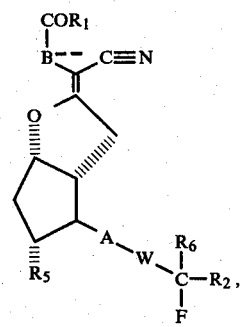

wherein
R$_1$ is OR$_3$ wherein R$_3$ is hydrogen or alkyl of 1–10 carbon atoms, or R$_1$ is NHR$_4$ wherein R$_4$ is alkanoyl or alkanesulfonyl,
B is alkylene of 1–5 carbon atoms,
A is —CH$_2$—CH$_2$—, cis—CH=CH—, or trans—CH=CH—,
W is hydroxymethylene or

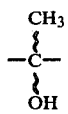

wherein the OH-group is optionally substituted by alkanoyl of 1–4 carbon atoms and the free or substituted OH-group can be in the α- or β-position, $R_2$ is alkyl of 1–6 carbon atoms optionally substituted by phenyl, or $R_2$ is phenyl, $R_5$ is hydroxy optionally substituted by alkanoyl of 1–4 carbon atoms, $R_6$ is hydrogen, fluorine, or alkyl of 1–4 carbon atoms or when $R_3$ is hydrogen, a salt thereof with a physiologically compatable base.

2. A compound of claim 1 wherein $R_4$ is $C_{1-10}$-alkanoyl or $C_{1-4}$ alkanesulfonyl.

3. 5-Cyano-16-fluoroprostacyclin methyl ester 11,15-diacetate.

4. 5-Cyano-16-fluoroprostacyclin methyl ester.

5. 5-Cyano-16-fluoroprostacyclin.

6. 5-Cyano-16-fluoro-20-methylprostacyclin methyl ester 11,15-diacetate.

7. 5-Cyano-16-fluoro-20-methylprostacyclin methyl ester.

8. 5-Cyano-16-fluoro-20-methylprostacyclin.

9. 5-Cyano-16-fluoro-15-methylprostacyclin.

10. 5-Cyano-16-fluoro-16-methylprostacyclin.

11. 5-Cyano-16-fluoro-N-methanesulfonylprostacyclin carboxamide a compound of claim 1.

12. 5-Cyano-16-fluoro-20-methyl-N-acetylprostacyclin carboxamide.

13. 5-Cyano-16,16-difluoroprostacyclin.

14. A pharmaceutical composition comprising an amount of a compound of claim 1 effective to lower blood pressure and a pharmaceutically acceptable carrier.

15. A method of lowering blood pressure in a patient in need of such treatment comprising administering to the patient an amount of a compound of claim 1 effective to lower blood pressure.

* * * * *